United States Patent

Benoit et al.

[11] Patent Number: 5,164,409
[45] Date of Patent: Nov. 17, 1992

[54] PYRROLES POSSESSING INSECTICIDAL ACTIVITY

[75] Inventors: Marc Benoit, Roquevaire; Jacques Demassey, Montevrain; Jean-Pierre Demoute, Neuilly Plaisance; Jean Tessier, Vincennes, all of France

[73] Assignee: Roussel Uclaf, Paris, France

[21] Appl. No.: 661,399

[22] Filed: Feb. 26, 1991

[30] Foreign Application Priority Data

Feb. 27, 1990 [FR] France .................. 90 02405

[51] Int. Cl.$^5$ .................. A01N 43/36; C07D 207/30
[52] U.S. Cl. .................. 514/427; 548/562; 548/561
[58] Field of Search .......... 548/562; 514/427

[56] References Cited

U.S. PATENT DOCUMENTS 4,737,513  4/1988  Tessier et al. .................. 514/427
4,798,901  1/1989  Tessier et al. .................. 548/330

OTHER PUBLICATIONS

CA 105:172784m Pyrrolylmethyl cyclopropanecarboxylates, Tessier et al., p. 774, 1986.
CA 106:50507y Pyrrolylmethyl chrysanthamates as pesticides (insectides), Tessier et al., p. 672, 1986.
CA 110:231924k New pyrethroids . . . preparation, Demassey et al., p. 678, 1988.

Primary Examiner—Joseph Paul Brust
Assistant Examiner—Joseph K. McKane
Attorney, Agent, or Firm—Bierman and Muserlian

[57] ABSTRACT

All possible stereoisomers and mixtures of a compound of the formula

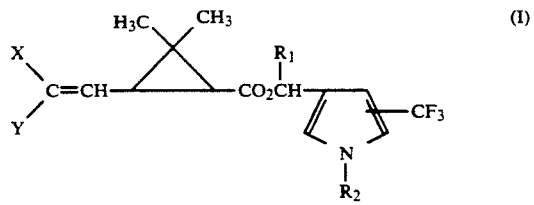

wherein X and Y are different and are selected from the group consisting of hydrogen, halogen, —CN, alkyl and haloalkyl of 1 to 8 carbon atoms and phenyl optionally substituted by at least one member of the group consisting of halogen and alkyl and alkoxy of 1 to 8 carbon atoms, $R_1$ is selected from the group consisting of hydrogen, methyl, —CN and ethynyl,

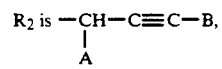

A and B are individually selected from the group consisting of hydrogen, halogen, alkyl of 1 to 8 carbon atoms and aryl of 6 to 14 carbon atoms and the —CF$_3$ is in the 2-, 4- or 5-position of the pyrrole ring having pesticidal activity.

18 Claims, No Drawings

PYRROLES POSSESSING INSECTICIDAL ACTIVITY

STATE OF THE ART

Related prior art includes U.S. Pat. Nos. 4,737,513 and 4,798,901, U.S. Pat. Nos. 4,166,063; 4,513,147; and 4,281,182; U.S. Pat. No. 4,565,822; U.S. Pat. No. 4,920,231 and U.S. patent application Ser. No. 165,585 filed Mar. 8, 1988.

OBJECTS OF THE INVENTION

It is an object of the invention to provide the novel compounds of formula I and a process for their preparation.

It is another object of the invention to provide novel pesticidal compositions and a novel method of combatting pests.

These and other objects and advantages of the invention will become obvious from the following detailed description.

THE INVENTION

The novel compounds of the invention are all possible stereoisomers and mixtures of a compound of the formula

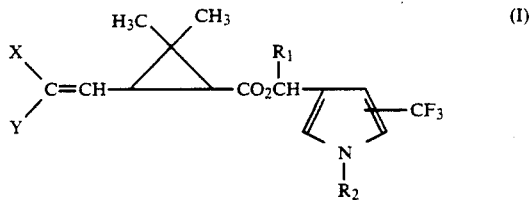

wherein X and Y are different and are selected from the group consisting of hydrogen, halogen, —CN, alkyl and haloalkyl of 1 to 8 carbon atoms and phenyl optionally substituted by at least one member of the group consisting of halogen and alkyl and alkoxy of 1 to 8 carbon atoms, $R_1$ is selected from the group consisting of hydrogen, methyl, —CN and ethynyl, $R_2$ is —CH—C≡C—B, A and B are individually selected from the group consisting of hydrogen, halogen, alkyl of 1 to 8 carbon atoms and aryl of 6 to 14 carbon atoms and the —$CF_3$ is in the 2-, 4- or 5- position of the pyrrole ring.

When X or Y is halogen, it is preferably fluorine, chlorine or bromine. When X or Y is alkyl, it is preferably methyl, ethyl or n-propyl. When X or Y is alkyl substituted by one or more halogens, it is preferably —$CF_3$ or —$CHF_2$. When X or Y is phenyl substituted by one or more halogens, it is preferably 4-chloro phenyl. When X or Y is phenyl substituted by one or more alkyls, it is preferably phenyl substituted by one or more of methyl, ethyl, n-propyl or isopropyl. When X or Y is phenyl substituted by one or more alkoxys, it is preferably phenyl substituted by one or more of methoxy or ethoxy.

When A or B is halogen, it is preferably fluorine, chlorine or bromine. When A or B is alkyl, it is preferably methyl, ethyl, n-propyl or isopropyl. When A or B is aryl, it is preferably phenyl.

Among the preferred compounds of formula I are those wherein X is —$CF_3$ or fluorine, those wherein Y is chlorine, those wherein $R_1$ is hydrogen, those wherein $R_2$ is propargyl and those wherein the —$CF_3$ is in the 2-position in their various stereoisomer forms and mixtures. Preferably, the cyclopropane copula has the (1R, cis) structure.

Among the specific preferred compounds of the invention are [1-(2-propynyl)-2-(trifluoromethyl)-1H-pyrrol-3-yl] methyl [1R-[1α,3α(Z)]]-3-(2-chloro-3,3,3-trifluoro-1-propenyl)- 2,2-dimethyl cyclopropanecarboxylate, [1-(2-propynyl)-2-(trifluoromethyl)-1 H-pyrrol-3-yl]- methyl [1R-[1α,3α(E+Z)]]-3-(2-chloro-2-fluoro-ethenyl)-2,2-dimethyl cyclopropanecarboxylate, [1-(2-propynyl)-2-(trifluoromethyl)-1H-pyrrol-3-yl]-methyl [1R-[1α,3α(E+Z)]]-3-(2-chloro-2-fluoro-ethenyl)-2,2-dimethyl cyclopropanecarboxylate, [1-(2-propynyl)-2-(trifluoromethyl)-1H-pyrrol-3-yl]-methyl [1R-[1α,3α(E+Z)]]-3-(2-chloro-ethenyl)-2,2-dimethyl cyclopropanecarboxylate and [1-(2-propynyl)-2-(trifluoromethyl)-1H-pyrrol-3-yl]-methyl [1R-[1α,3α(E)]]-3-(2-cyano-2-fluoro ethenyl)-2,2-dimethyl cyclopropanecarboxylate.

The pesticidal compositions of the invention are comprised of a pesticidally effective amount of at least one compound of formula I and an inert carrier. The compositions are useful against parasites of vegetation whether sub-soil or super-soil parasites and parasites of warm-blooded animals and the premises and can be used against insects, nematodes and acarides of vegetation and warm-blooded animals.

The compositions may also be used to combat insects and other parasites of the soil, for example, Coleoptera such as DIABROTICA, click beetles and cockchafer grubs, Myriapoda such as scutigeridae and blanjules, Diptera such as gall midges and Lepidoptera such as owlet moths. They are used at doses of between 10 g and 300 g of active material per hectare.

The compositions can also be used to combat insects in premises, notably to combat flies, mosquitoes and cockroaches. Moreover, the compositions are photostable and less toxic to mammals. All these properties make the compositions which correspond perfectly to the demands of the modern agrochemical industry as they allow the protection of crops while preserving the environment.

The compositions can also be used to combat parasitic acaridae and nematodes of vegetation and can also be used to combat parasitic acaridae of animals, to combat, for example, ticks and notably ticks of the Boophilus species, those of the Hyalomnia species, those of the Amblyomnia species and those of the Rhipicephalus species or to combat all sorts of mites and notably the sarcoptic mite, the psoroptic mite and the chorioptic mite.

Particularly preferred are insecticide compositions containing as active ingredient at least one of the products defined above.

The compositions of the invention are prepared by the usual processes of the agrochemical industry or the veterinary industry or the animal feed products industry. These compositions can be in the form of powders, granules, suspensions, emulsions, solutions, aerosol solutions, combustible strips, baits or other preparations usually employed for the use of this type of compound.

In addition to the active ingredient, the compositions may contain a vehicle and/or a nonionic surface active agent, ensuring, moreover, a uniform dispersion of the components of the mixture. The vehicle used can be a liquid such as water, alcohol, hydrocarbons or other organic solvents, a mineral, animal or vegetable oil, a powder such as talc, clays, silicates, kieselguhr or a combustible solid.

The insecticide compositions of the invention contain preferably 0.005% to 10% by weight of active material. According to an advantageous operating method, for use in premises, the compositions of the invention are used in the form of fumigant compositions.

The compositions of the invention can then be advantageously composed of, for the non-active part, a combustible insecticide serpentine (or coil), or also an incombustible fibrous substrate. In the latter case, the fumigant obtained after incorporation of the active ingredient is placed on a heating apparatus such as an electric emanator.

In the case where an insecticide serpentine is used, the inert support can be comprised of Pyrethrum marc, Tabu powder (or Machilus thumbergii leaf powder), Pyrethrum stem powder, cedar leaf powder, sawdust (such as pine sawdust), starch and coconut shell powder. The dose of active ingredient can then be, for example, 0.03 to 1% by weight. In the case where an incombustible fibrous support is used, the dose of active ingredient can then be 0.03 to 95% by weight.

The compositions of the invention for use in premises can also be obtained by preparing a sprayable oil based on the active ingredient, this oil soaking a lamp wick and then being set alight. The concentration of active ingredient incorporated in the oil is preferably 0.03 to 95% by weight.

The acaricide and nematocide compositions contain as active ingredient at least on of the products of formula 1, as defined above. The insecticide compositions of the invention, as acaricide and nematocide compositions, can optionally have other pesticide agents added to them. The acaricide and nematocide compositions can be presented preferably in the form of powder, granules, suspensions, emulsions or solutions.

For acaricide use, wettable powders are preferably used for foliar spraying and contain 1 to 80% of active ingredient or liquids for foliar spraying containing 1 to 500 g/l of active ingredient. Powders for foliar dusting containing 0.05% to 3% of active ingredient can also be used.

For nematocide use, liquids for soil treatment containing 300 to 500 g/l of active ingredient are preferably used. The acaricide and nematocide compositions of the invention are used, preferably, at doses comprised between 1 and 100 g of active ingredient per hectare.

To increase the biological activity of the products of the invention, there can be added standard synergists used in such cases such as 1-(2,5,8-trioxadodecyl)-2-propyl-4,5-methylenedioxy benzene (or piperonyl butoxide) or N-(2-ethyl-heptyl)-bicyclo-[2,2-1]-5-heptene-2,3-dicarboximide, or piperonyl-bis-2-(2'-n-butoxy-ethoxy) ethylacetal (or tropital).

The compounds of formula I show an excellent general tolerance, and therefore are useful to combat affections caused by ticks and mites in humans and animals, especially to combat lice as a preventative or curative and to combat mites.

The compositions of the invention can be administered externally by spraying, by shampoo, by bathing or painting on. The compositions for veterinary use can also be administered by painting the dorsal spine by the "pour-on" method.

It can also be mentioned that the compositions of the invention can be used as biocides or as growth regulators.

Also a subject of the invention are combinations endowed with insecticide, acaricide or nematocide activity, characterized in that they contain as active ingredient at least one of the compounds of formula I and at least one of the pyrethrinoid esters chosen from the group consisting of the esters of allethrone, of 3,4,5,6-tetrahydrophthalimidomethyl alcohol, of 5-benzyl-3-furyl methyl alcohol, of 3-phenoxybenzyl alcohol and of α-cyano-3-phenoxybenzyl alcohols with chrysanthemic acids, by the esters of 5-benzyl-3-furyl methyl alcohol with 2,2-dimethyl-3-(2-oxo-3-tetrahydrothiophenylidenemethyl)-cyclopropane-1-carboxylic acids, by the esters of 3-phenoxybenzyl alcohol and of α-cyano-3-phenoxybenzyl alcohols with 2,2-dimethyl-3-(2,2-dichlorovinyl)-cyclopropane-1-carboxylic acids, by the esters of α-cyano-3-phenoxybenzyl alcohols with 2,2-dimethyl-3-(2,2-dibromovinyl)-cyclopropane-1-carboxylic acids, by the esters of 3-phenoxybenzyl alcohols with 2-parachlorophenyl-2-isopropyl acetic acids, by the esters of allethrolones, of 3,4,5,6-tetrahydrophthalimidomethyl alcohol, of 5-benzyl-3-furyl methyl alcohol, of 3-phenoxybenzyl alcohol, and of α-cyano-3-phenoxybenzyl alcohol with 2,2-dimethyl-3-(1,2,2,2-tetrahaloethyl)-cyclopropane-1-carboxylic acids, in which "halo" represents a fluorine, chlorine or bromine atom, it being understood that the compounds I can exist in all their possible stereoisomer forms as well as the acid and alcohol copulas of the above pyrethrinoid esters.

The novel method of the invention for combatting parasites comprises contacting parasites with a parasitically effective amount of at least one compound of formula I. The method is particularly effective against insects.

The process for the preparation of the compounds of formula I comprises reacting an acid of the formula

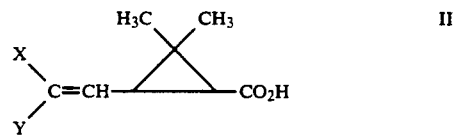

wherein X and Y have the above definitions or a functional derivative of the acid with an alcohol of the formula

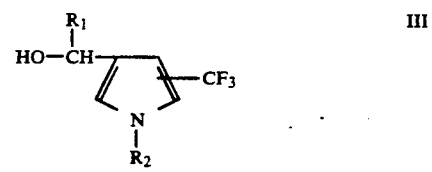

wherein $R_1$ and $R_2$ have the above meaning to obtain the corresponding compound of formula I.

The compounds of formula II are known products (cf for example EP 0,335,801; 0,133,406; 19,787; 10,859; 61,114 or French Patent No. 2,185,612). The alcohols of formula III are also known products (for example European Patent No. 0,176,386).

In the following examples, there are described several preferred embodiments to illustrate the invention. However, it should be understood that the invention is not intended to be limited to the specific embodiments.

EXAMPLE 1

[1-(2-propynyl)-2-(trifluoromethyl)-1H-pyrrol-3-yl]-methyl [1R-[1α,3α(Z)]]-3-(2-chloro-3,3,3-trifluoro-1-propenyl)-2,2-dimethyl cyclopropanecarboxylate A solution of 450 mg of 1-(2-propynyl)-2-(trifluoromethyl)-1H-pyrrol-3-methanol, 410 mg of [1R-[1α,3α(Z)]]-3-(2-chloro-3,3,3-trifluoro-1-propenyl)-2,2-dimethyl cyclopropanecarboxylic acid and 8 ml of anhydrous methylene chloride was cooled to 0° C. and a solution of 345 mg of dicyclohexylcarbodiimide, 20 mg of dimethylaminopyridine and 10 ml of methylene chloride was added at 0° C. to the solution. The reaction mixture was allowed to return to ambient temperature and was stirred for 2 hours. After filtering, the filtrate was concentrated and the residue was taken up in isopropyl ether. The insoluble part was eliminated by filtration and the filtrate was concentrated. Chromatography was carried out on silica eluting with a hexane - ethyl acetate (9-1) mixture to obtain 618 mg of the expected product (85% yield) with a specific rotation of $[\alpha]_D = +15.5° \pm 2°$ (c 32 0.5% in CHCl$_3$).

Using the procedure of Example 1, the appropriate acids and 1-(2-propynyl)-2-(trifluoromethyl)-1H-pyrrol-3-methanol were reacted to obtain the following products:

EXAMPLE 2

[1-(2-propynyl)-2-(trifluoromethyl)-1H-pyrrol-3-yl]-methyl, [1R-[1α,3α(E+Z)]]-3-(2-chloro-2-fluoro-ethenyl)-2,2-dimethyl cyclopropanecarboxylate with a specific rotation of $[\alpha]_D = +6.5° \pm 1.5°$ (c=0.5% in CHCl$_3$).

EXAMPLE 3

[1-(2-propynyl)-2-(trifluoromethyl)-1H-pyrrol-3-yl]-methyl [1R-[1α,3β(E+Z)]]-3-(2-chloro-2-fluoro-ethenyl)-2,2-dimethyl cyclopropanecarboxylate with a specific rotation of $[\alpha]_D = -25.5° \pm 2.5°$ (c=0.35% in CHCl$_3$).

EXAMPLE 4

[1-(2-propynyl)-2-trifluoromethyl)-1H-pyrrol-3-yl]-methyl [1R-[1α,3α(E+Z)]]-3-(2-chloro-ethenyl)-2,2-dimethyl cyclopropanecarboxylate with a specific rotation of $[\alpha]_D = +16.5° \pm 2°$ (c=0.4% in CHCl$_3$).

EXAMPLE 5

[1-(2-propynyl)-2-(trifluoromethyl)-1H-pyrrol-3-yl]-methyl [1R-[1α,3α(E)]]-3-(2-cyano-2-fluoro-ethenyl)-2,2-dimethyl cyclopropanecarboxylate with a specific rotation of $[\alpha]_D = +30° \pm 1.5°$ (c=1% in toluene).

EXAMPLE 6

[1-(2-propynyl)-2-(trifluoromethyl)-1H-pyrrol-3-yl]methyl [1R-[1α,3α(Z)]]-3-(2-cyano-2-fluoro-ethenyl)-2,2-dimethyl cyclopropanecarboxylate.

EXAMPLE 7

[1-(2-propynyl)-2-(trifluoromethyl)-1H-pyrrol-3-yl]methyl [1R-[1α,3β(Z)]]-3-[2-chloro-[3-(4-chlorophenyl-1-ethenyl)]-2,2-dimethyl cyclopropanecarboxylate.

Using the procedure of Example 1, the appropriate acids and the appropriate alcohols were reacted to obtain the following products:

EXAMPLE 8

[1-(2-propynyl)-4-(trifluoromethyl)-1H-pyrrol-3-yl]methyl [1R-[1α,3α(Z+E)]]-3-(2-chloro-2-fluoro-ethenyl)-2,2-dimethyl cyclopropanecarboxylate with a specific rotation of $[\alpha]_D = -18.5° \pm 2.5°$ (c=0.3% in CHCl$_3$).

EXAMPLE 9

[1-(2-propynyl)-4-(trifluoromethyl)-1H-pyrrol-3-yl]methyl [1R-[1α,3α(Z)]]-3-(2-chloro-2,2,2-trifluoromethyl-ethenyl]-2,2-dimethyl cyclopropanecarboxylate with a specific rotation of $[\alpha]_D = +15.5° \pm 2.5°$ (c=0.5% in CHCl$_3$).

EXAMPLE 10

[1-(2-propynyl)-5-(trifluoromethyl)-1H-pyrrol-3-yl] methyl [1R-[1α,3α(Z+E)]]-3-(2-chloro-2-fluoro-ethenyl)-2,2-dimethyl cyclopropanecarboxylate with a specific rotation of $[\alpha]_D = +12° \pm 2°$ (c=0.5% in CHCl$_3$).

EXAMPLE 11

[1-(2-propynyl)-5-(trifluoromethyl)-1H-pyrrol-3-yl] methyl [1R-[1α,3α(Z)]]-3-(2-chloro-2-trifluoromethyl-ethenyl)-2,2-dimethyl cyclopropanecarboxylate with a specific rotation of $[\alpha]_D = +25° \pm 2°$ (c=0.5% in CHCl$_3$).

EXAMPLE 12

Preparation of a Soluble Concentrate

A homogeneous mixture was prepared containing:

| | |
|---|---|
| Product of Example 1 | 0.25 g |
| Piperonyl butoxide | 1.00 g |
| Tween 80 | 0.25 g |
| Topanol A | 0.1 g |
| Water | 98.4 g |

EXAMPLE 13

Preparation of an Emulsifiable Concentrate

The following were intimately mixed:

| | |
|---|---|
| Product of Example 2 | 0.015 g |
| Piperonyl butoxide | 0.5 g |
| Topanol A | 0.1 g |
| Tween 80 | 3.5 g |
| Xylene | 95.885 g |

EXAMPLE 14

Preparation of an Emulsifiable Concentrate

A homogeneous mixture was prepared containing:

| | |
|---|---|
| Product of Example 1 | 1.5 g |
| Tween 80 | 20.00 g |
| Topanol A | 0.1 g |
| Xylene | 78.4 g |

EXAMPLE 15

Preparation of a Fumigant Composition

The following were mixed together in a homogeneous manner:

| | |
|---|---|
| Product of Example 1 | 0.25 g |
| Tabu powder | 25.00 g |
| Cedar leaf powder | 40.00 g |
| Pine sawdust | 33.75 g |
| Brilliant green | 0.5 g |
| p-Nitrophenol | 0.5 g |

BIOLOGICAL STUDY

A. Study of the Knock-Down Effect on the Household Fly

The test insects were 4-day old female household flies and the operation was carried out by direct spraying in a Kearns and March chamber at a concentration of 0.10 g/l or 1 g/l using a mixture of acetone (5%0 and Isopar L (petroleum solvent) as solvent (quantity of solvent used 2 ml per second). 50 insects were used per treatment and checks were carried out every minute up to 10 minutes, then at 15 minutes and the $KT_{50}$ was determined by the usual methods.

The experimental results obtained are summarized in the following table:

| Compounds | Concentration (g/l) | $KT_{50}$ in mn |
|---|---|---|
| EXAMPLE 1 | 0.1 | 10.4 |
| EXAMPLE 2 | 0.1 | 3.1 |
| EXAMPLE 3 | 0.1 | 5.2 |
| EXAMPLE 4 | 0.1 | 3.9 |
| EXAMPLE 6 | 0.1 | 2.4 |
| EXAMPLE 8 | 1 | 3.2 |
| EXAMPLE 9 | 1 | 5.2 |
| EXAMPLE 10 | 1 | 6.8 |

B. Study of the Lethal Effect on Various Insects a) Study of the Lethal Effect on the Household Fly

The test insects were 4 to 5 day old female household flies and the operation was carried out by topical application of 1 microliter of an acetone solution on the dorsal thorax of the insects using an Arnold micromanipulator. 30 individuals were used per treatment and the mortality check was carried out twenty four hours after treatment. The results obtained expressed as $LD_{50}$ or dose (in nanograms) per individual required to kill 50% of the insects, are as follows:

| Compounds | $LD_{50}$ in ng/insect |
|---|---|
| EXAMPLE 1 | 8.3 |
| EXAMPLE 2 | 10.2 |
| EXAMPLE 3 | 11.8 | b) Study of the lethal effect on *Spodoptera littoralis* larvae

The test were carried out by topical application of an acetone solution on the dorsal thorax of the larvae using an Arnold micromanipulator with 15 larvae being used per dose of the test product. The larvae used were fourth-stage larvae, that is to say aged about 10 days having been reared at 24° C. and 65% relative humidity. After treatment, the individuals were placed on a nutritive artificial medium (Poitout medium) and the mortality check was carried out 48 hours after treatment. The experimental results are summarized in the following table:

| Compounds | $LD_{50}$ in ng/insect |
|---|---|
| EXAMPLE 1 | 11.2 |
| EXAMPLE 2 | 16.6 |
| EXAMPLE 3 | 38.4 |
| EXAMPLE 6 | 30.2 | c) Study of the activity on Diabrotica

The test insects were final stage larvae of *Diabrotica undecimpunctata*. A 9 cm disc of filter paper placed at the bottom of a Petri dish was treated using 1 ml of an acetone solution. After drying, 15 larvae per dose were deposited and the mortality check was carried out 24 hours after treatment. The lethal dose 100 ($LD_{100}$) expressed in mg/liter was determined. The results were the following:

| | |
|---|---|
| Product of Example 1 | 0.6 |
| Product of Example 2 | 0.3 |
| Product of Example 3 | >10 |
| Product of Example 4 | 5 |

C) Study of the Activity on *Aphis cracivora*

2 ml of a water-acetone (50/50) solution was sprayed on bean leaves (vicia fabae) until the surface was covered with solution. After drying, 15 suitable females of *Aphis cracivora* were deposited and the group was kept on damp filter paper inside a Petri dish. 24 hours after the initiation of contact, the determination of the number of dead insects was carried out.

| Compounds | $LC_{50}$ in mg/l |
|---|---|
| Example 1 | 0.15 |
| Example 2 | 0.30 |
| Example 3 | 2.98 |
| Example 4 | 2.60 |
| Example 5 | 1.52 |
| Example 6 | 0.76 |

Various modifications of the process and the products of the invention may be made without departing from the spirit or scope thereof and it is to be understood that the invention is intended to be limited only as defined in the appended claims.

What we claim is:

1. All possible stereoisomers and mixtures of a compound of the formula

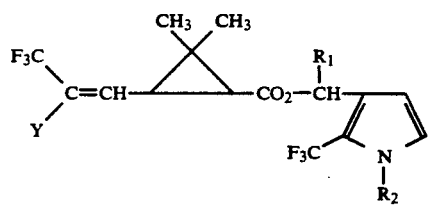

wherein Y is selected from the group consisting of hydrogen, halogen, —CN, alkyl and haloalkyl of 1 to 8 carbon atoms and phenyl optionally substituted by at least one member of the group consisting of halogen and alkyl and alkoxy of 1 to 8 carbon atoms, $R_1$ is selected from the group consisting of hydrogen, methyl, —CN and ethynyl,

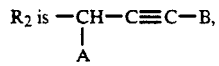

A and B are individually selected from the group consisting of hydrogen, halogen, alkyl of 1 to 8 carbon atoms and aryl of 6 to 14 carbon atoms.

2. A compound of claim 1 wherein Y is —Cl.

3. A compound of claim 1 wherein $R_1$ is hydrogen.

4. A compound of claim 1 wherein $R_2$ is propargyl.

5. A compound of claim 1 wherein the cyclopropane copula has (1R, cis) structure.

6. An insecticidal composition comprising an insecticidally effective amount of at least one compound of claim 1 and an inert carrier.

7. A composition of claim 6 wherein Y is —Cl.

8. A composition of claim 6 wherein $R_1$ is hydrogen.

9. A composition of claim 6 wherein $R_2$ is propargyl.

10. A composition of claim 6 wherein cyclopropane copula has (1R, cis) structure.

11. A method of combatting insects comprising contacting insects with an insecticidally effective amount of at least one compound of claim 1.

12. A method of claim 11 wherein Y is —Cl.

13. A method of claim 11 wherein $R_1$ is hydrogen.

14. A method of claim 11 wherein $R_2$ is propargyl.

15. A method of claim 11 wherein the cyclopropane copula has (1R, cis) structure.

16. A compound of claim 1 which is [1-(2-propynyl)-2-(trifluoromethyl)-1H-pyrrol-3yl] methyl [1R-[1α,3α(Z)]]-3-(2-chloro-3,3,3-trifluoro-1-propenyl)-2,2-dimethyl cyclopropanecarboxylate.

17. A composition of claim 6 wherein the active compound is [1-(2-propynyl-2-trifluoromethyl-1H-pyrrol-3yl]-methyl [1R-[1α,3α(2)]]-3-(2-chloro-3,3,3-trifluoro-1-propenyl)-2,2-dimethyl-cyclopropane carboxylate.

18. A method of claim 11 wherein the active compound is [1-(2-propynyl-2-trifluoromethyl-1H-pyrrol-3-yl]-methyl [1R-[1α,3α(2)]]-3-(2-chloro-3,3,3-trifluoro-1-propenyl)-2,2-dimethyl-cyclopropane carboxylate.

* * * * *